United States Patent [19]
Lavin

[11] Patent Number: 5,219,282
[45] Date of Patent: * Jun. 15, 1993

[54] DENTAL CAST INDEXING FOR ACCURATE PLACEMENT OF ORTHODONTIC BRACKETS

[76] Inventor: Joseph J. Lavin, W. 508 - 7th Ave., Spokane, Wash. 99204

[ * ] Notice: The portion of the term of this patent subsequent to Nov. 12, 2008 has been disclaimed.

[21] Appl. No.: 790,411

[22] Filed: Nov. 7, 1991

Related U.S. Application Data

[63] Continuation-in-part of Ser. No. 458,302, Dec. 28, 1989, Pat. No. 5,064,368.

[51] Int. Cl.$^5$ .............................................. A61C 3/00
[52] U.S. Cl. .. ...................... 433/2; 433/213
[58] Field of Search .................. 433/2, 24, 53, 55, 56, 433/75, 76, 213

Primary Examiner—John J. Wilson
Attorney, Agent, or Firm—Wells, St. John, Roberts, Gregory & Matkin

[57] ABSTRACT

The invention described facilitates accurate placement of orthodontic brackets on a patient's mal-occluded teeth. An indexed dental cast of the patient's mal-occlusion is produced by the present apparatus. In process steps for indexing the crown model, various adjustment devices hold a selected mal-occluded crown model of the cast in an "ideal" or corrected position in space. The cast is thus positioned and held while a drill is used to form index holes in the cast material. The index holes record the "ideal" position of the selected crown model even though the crown model remains in its original mal-occluded position in the cast. Positioning of a bracket against the selected crown model is accomplished by a bracket holder and adapter using the index. The holder receives the bracket while the adapter is positioned, using probes inserted into the index holes. The holder may be moved to a selected tip angle and bracket placement height through adjustments on the adapter. The holder may also be precisely positioned to locate a bracket in a selected in and outs position in relation to the crown model.

20 Claims, 9 Drawing Sheets

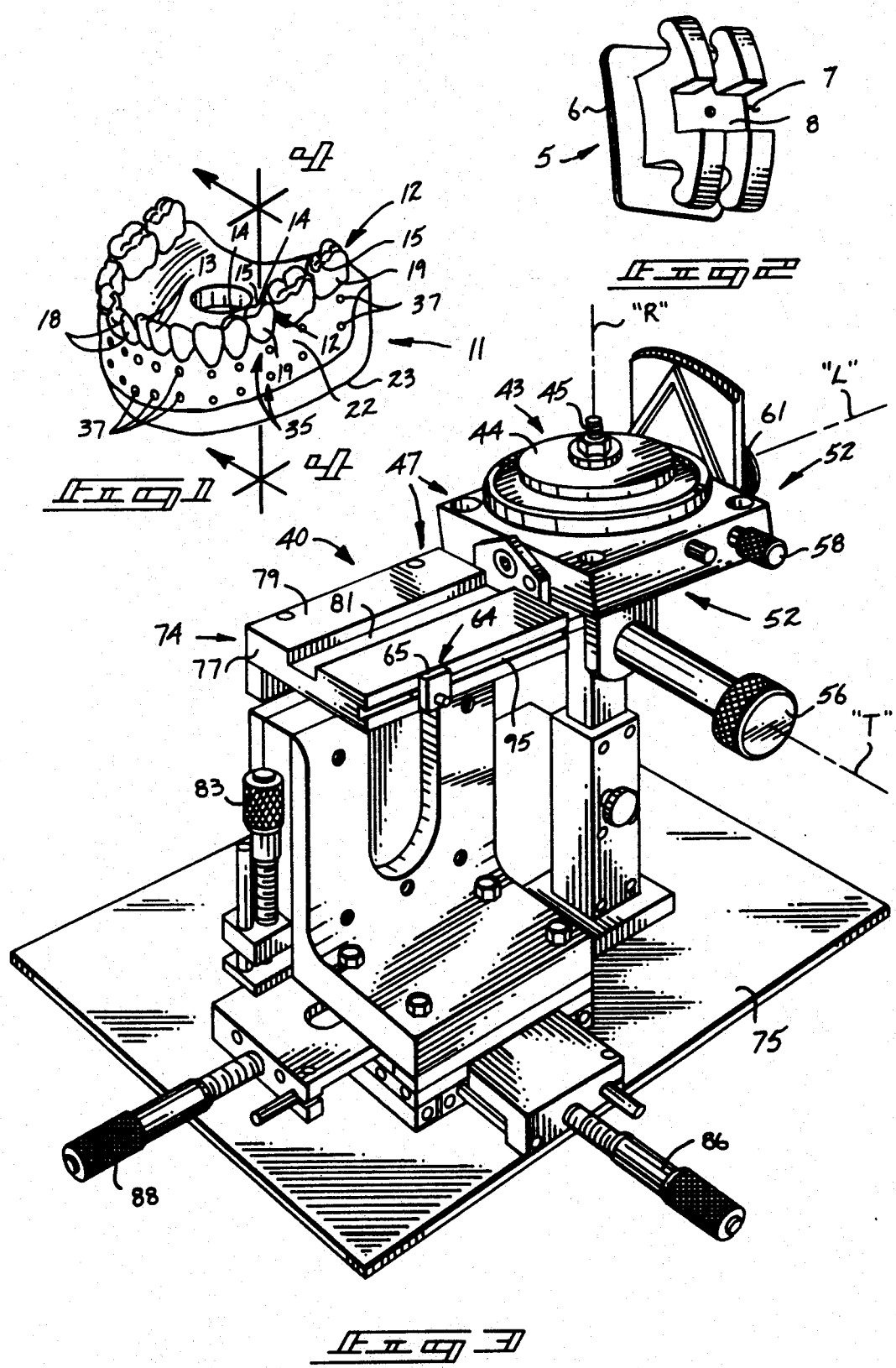

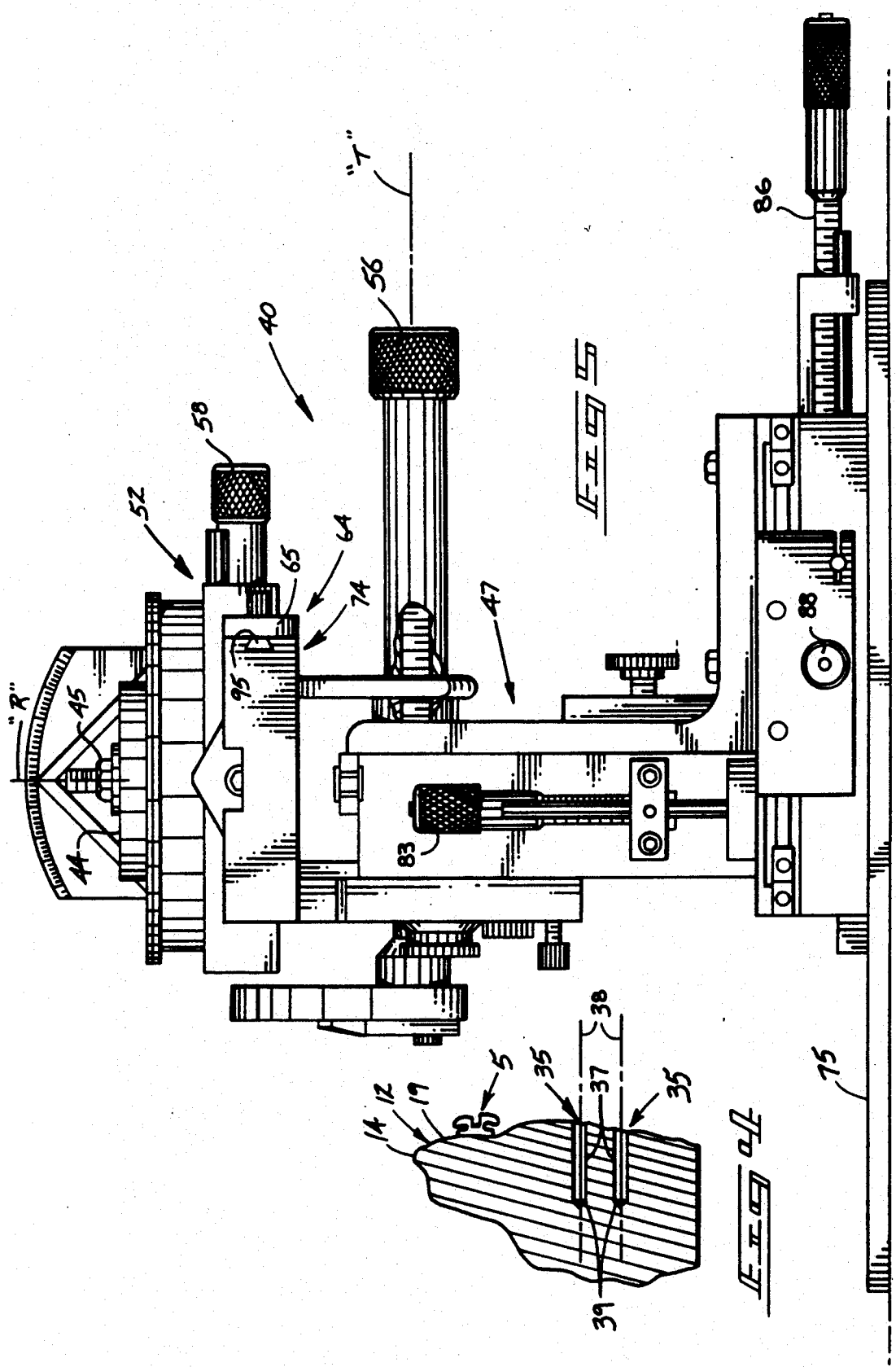

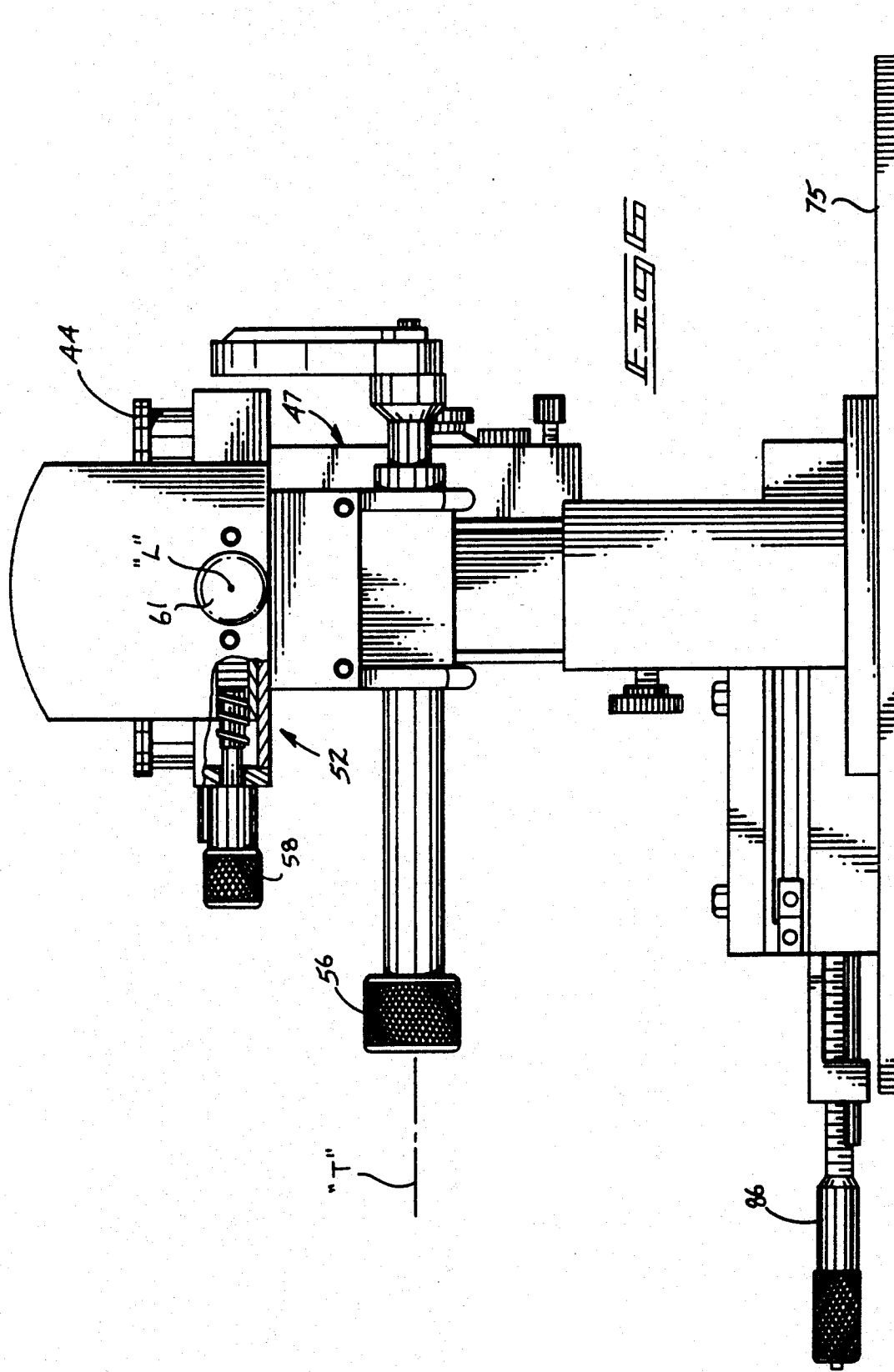

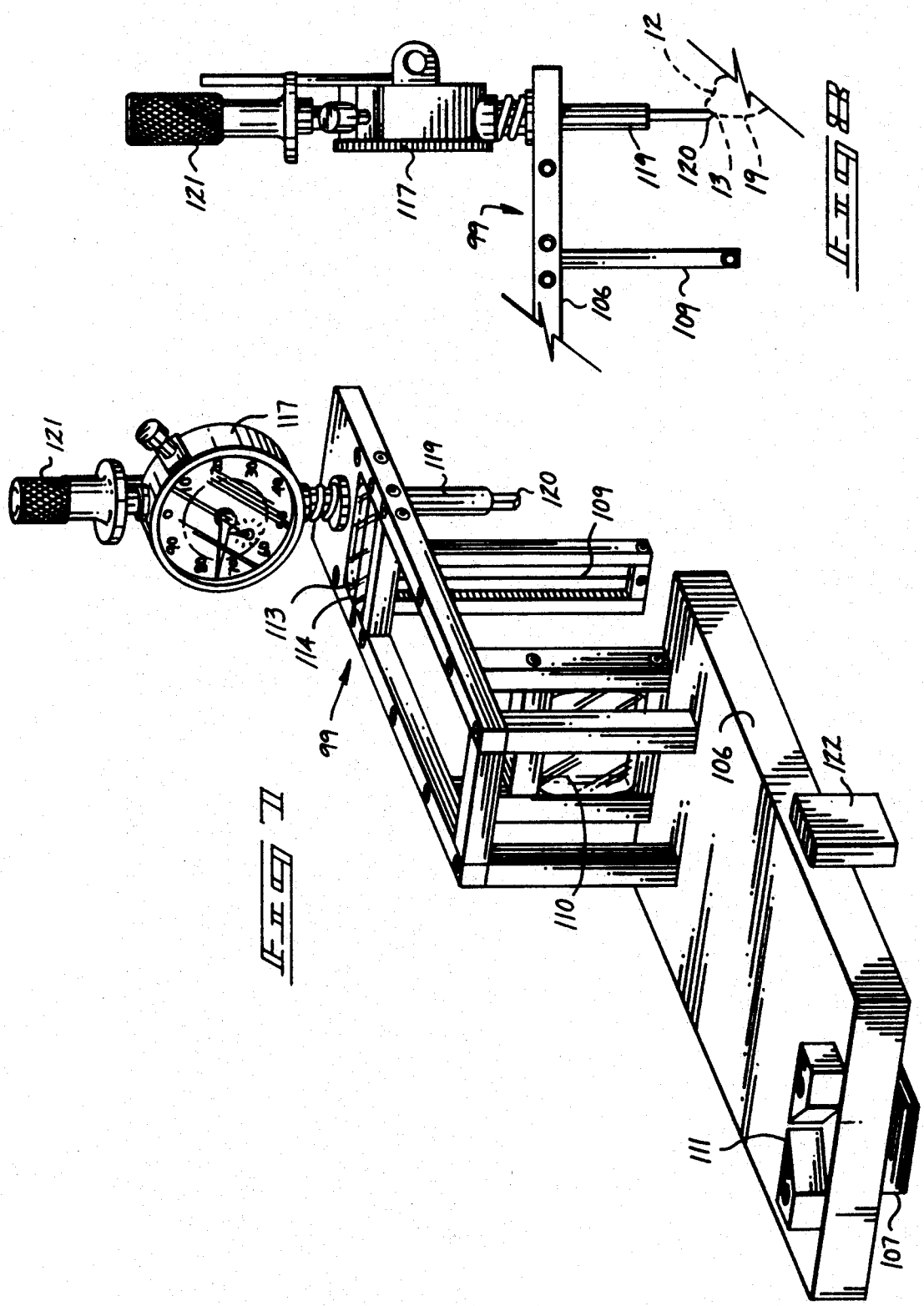

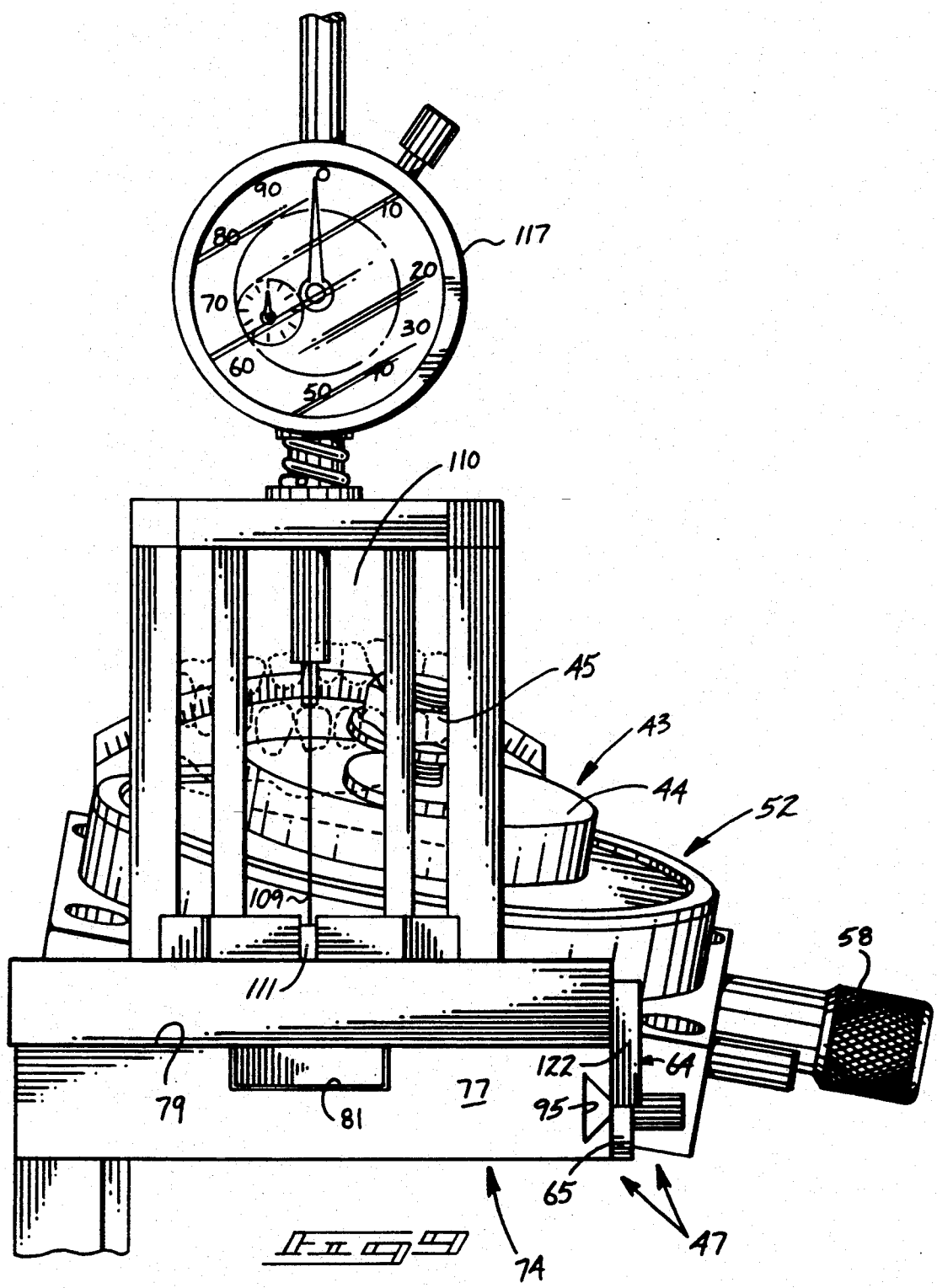

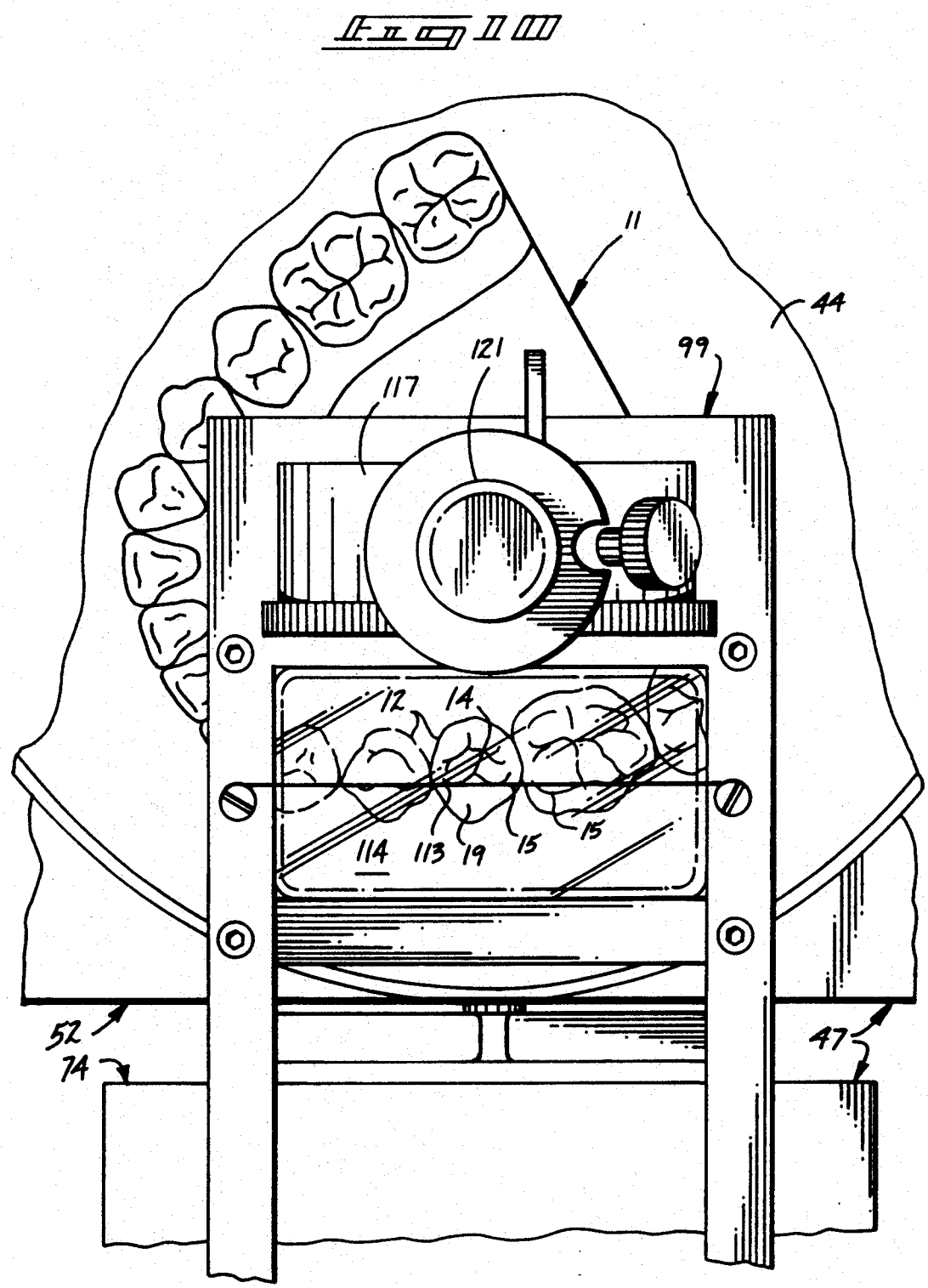

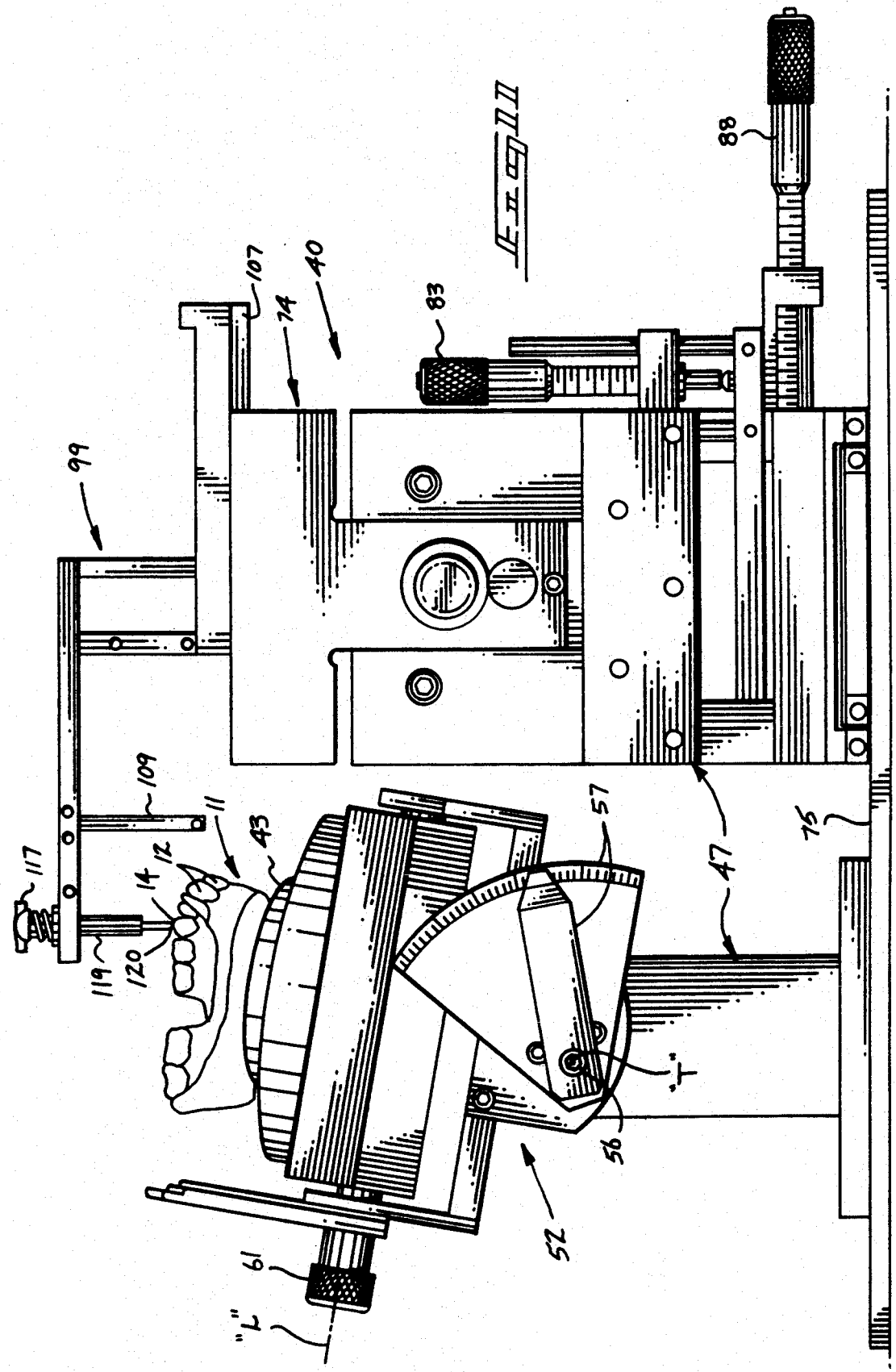

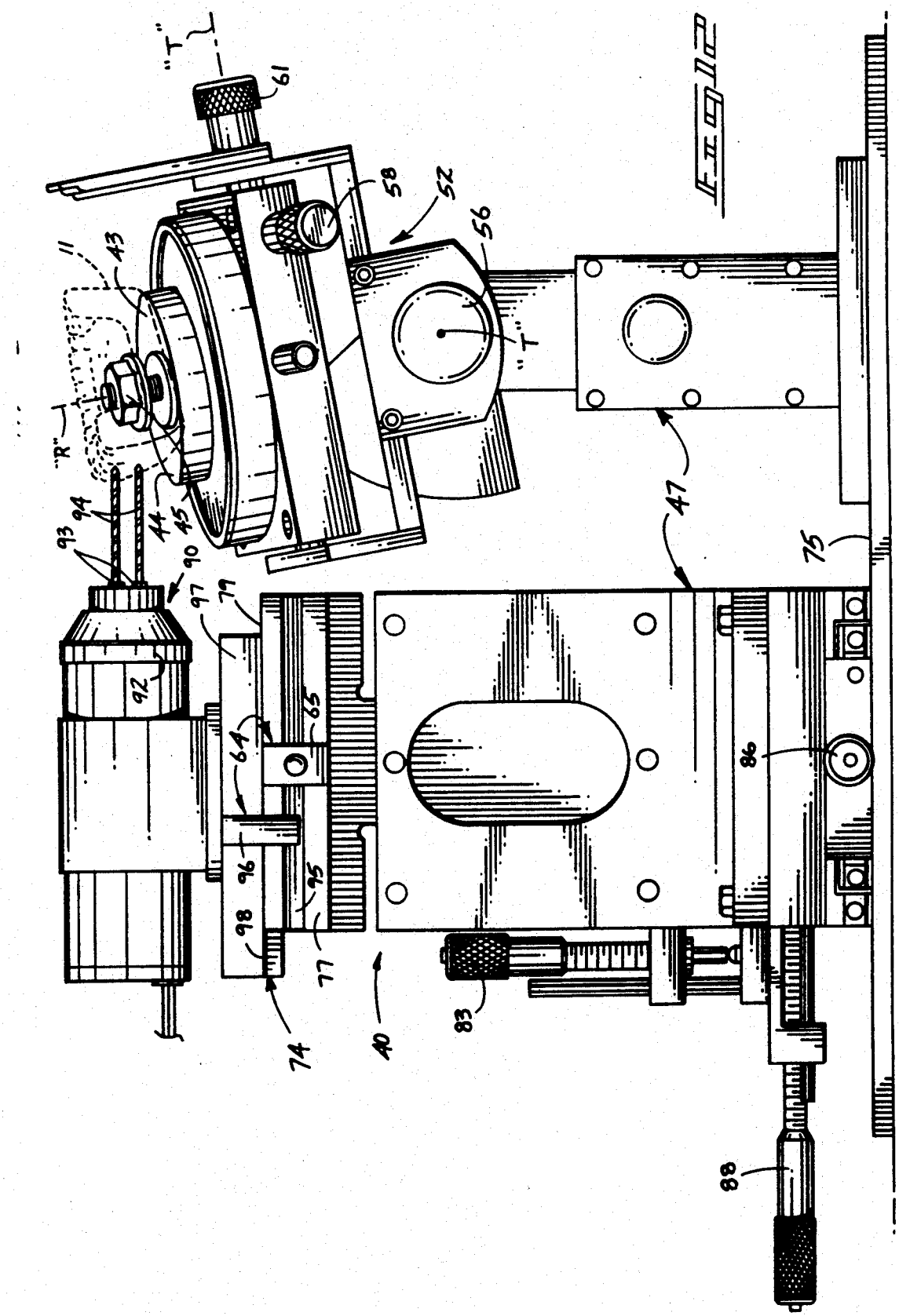

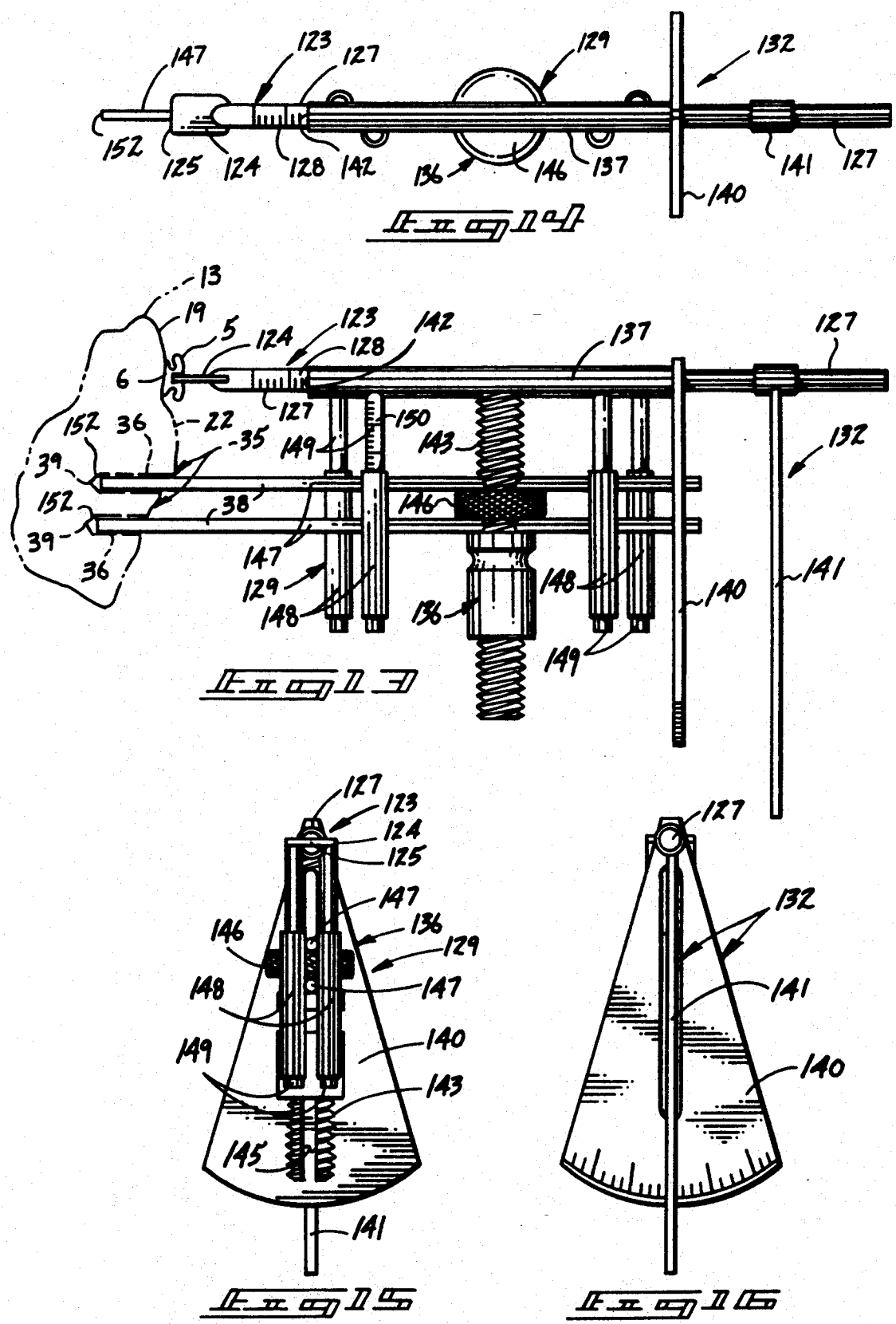

DENTAL CAST INDEXING FOR ACCURATE PLACEMENT OF ORTHODONTIC BRACKETS

RELATED APPLICATIONS

This is a continuation of application Ser. No. 458,302, filed on Dec. 28, 1989, and titled "Dental Cast Indexing for Accurate Placement of Orthodontic Brackets", now U.S. Pat. No. 5,064,368.

TECHNICAL FIELD

The present invention relates to the field of Orthodontics and more particularly to a system for recording information on a dental cast of a patient's mal-occlusion that will enable accurate placement of orthodontic brackets.

BACKGROUND OF THE INVENTION

Orthodontists are principally concerned with the straightening of irregular or "mal-occluded" teeth. Generally, the corrective technique first involves diagnosing the extent of the mal-occlusion and devising a course of treatment in which the teeth are to be repositioned into a desired arch configuration.

Once the diagnosis and treatment plan has been formulated, the orthodontists attaches orthodontic brackets on the crowns of the patient's teeth. It is often stated that one-third of total successful orthodontic treatment is the accurate placement of orthodontic brackets on the patent's mal-occluded teeth. This is because the orthodontic bracket which is usually constructed of metal, has a precision slot or receptacle that must be properly oriented in relation to the tooth upon which it is mounted. The precision slot or receptacle is typically between two and four millimeters in length and is rectangular in cross section to receive an arch wire. The arch wire is a curved length of spring wire that the orthodontist positions around the dental arch and secures it into the precision slot of each bracket previously mounted to selected crowns. The arch wire includes internal resiliency and "memory". The arch wire will therefore urge the brackets and attached teeth to move toward an "ideal" arch configuration.

Initially, small diameter arch wires are placed that loosely fit within the precision bracket slots. As the teeth begin to move toward a desired arch configuration, larger diameter arch wires may be placed. Ideally, a full size arch wire is eventually secured into each bracket on each tooth crown in the same dental arch.

Because the precision slots of the brackets and the larger arch wire are the same size and are rectangular in cross sectional shape, the arch wire controls the brackets and their attached tooth crowns in all planes of space. It is therefore desirable to have the bracket precisely positioned on the adjacent tooth in an "ideal" orientation on the tooth crown throughout the entire treatment term.

Generally, one of two methods is used to place brackets on the patient's teeth to accept the spring arch wires. These are the "direct" and the "indirect" bracket placement methods.

The direct method is perhaps the most popular yet the most inaccurate of the two methods. Using this method, the orthodontist attempts to center the bracket in a mesial-distal direction plus orient the precision slot of the bracket to the crowns in prescribed relationships to the teeth axes. This is done directly in the patient's mouth on each of the patient's teeth. The crowns of the teeth in a mal-occlusion are in disarray and it is both inefficient and frustrating for the orthodontist who must guess at proper bracket placement while controlling the lips, tongue and saliva of the patient. Often during the course of orthodontic treatment some brackets will have to be removed because of their inaccurate placement on the crowns and an attempt will be made again to more accurately place the brackets.

The direct method is completed without accurate knowledge of the precise position of the tooth in relation to a desired arch or "ideal" set-up. Further, in the direct method, visualization of the crown in an "ideal" set-up is done only by observation and hand manipulation. Inaccuracy of bracket placment is therefore a very real and probable result. Inaccurately placed brackets create difficulties in properly adapting arch wires and thus result in moving the teeth in undesirable directions.

The second method (namely the indirect method) though complicated, is more highly successful in eliminating some of the difficulties experienced with the direct method. Existing indirect methods usually involve initial bracket placement on a plaster "dental cast" of the patient's teeth, away from the patient in a laboratory atmosphere. In its most rudimentary form, the indirect method involves the same bracket placement procedures used for the direct method. The difference is that the brackets are first attached to a cast model of the mal-occlusion. The brackets are then removed from the model and placed on the patient's teeth. This process involves more patient comfort, less chair time and is therefore more effective than the direct method. However, it is still inefficient in that the Orthodontist or technician must mentally visualize the mal-occluded teeth in an "ideal" set-up before accurate placement of the brackets can be accomplished.

To solve some of these difficulties utilizing the indirect method, an "ideal" set-up can be attempted. An "ideal" set-up is a model formed by a procedure in which individual crown models plus four to five millimeters of the model gum tissue area below each crown is cut free of the base in the dental cast of the patient's mal-occlusion. Each crown model thus consists of a tooth crown and a section of the model gum area directly below the cast crown.

The individual crown models may then be reassembled on a wax rim shaped in the form of a dental arch. Sometimes, the individual crown and gum model sections are first mounted to pegs. The pegs are pressed into the wax to position the cast crown models in an arch configuration to complete the "ideal" set-up.

To make any change of crown model position in a set-up, a metal spatula is heated and then inserted into the wax around the section of the model gum area or around the peg, softening the wax and thus allowing the crown model to be altered in its position. The procedure is tedious and further lacks precision by requiring reliance only on rough, "eyeball" positioning of one crown model in relation to adjacent crown models.

U.S. Pat. No. 4,668,192, issued to the present applicant, discloses an apparatus and method for executing substantially more accurate orthodontic procedures utilizing a novel simulated root arrangement attached to individual crown models by an apparatus and procedure in which the simulated root is precisely oriented in relation to landmark locations identified on the above crown model. These crown models may be precisely positioned in an "ideal" set-up articulator.

A second cast may then be made to secure the various crown models in their "ideal" set-up. This set-up may be used with a bracket slot orienting and placement instrument for appropriate selection and placement of arch wire brackets on the individual tooth models.

Mechanisms are provided to indicate bracket thickness and backing curvature so the precision slots of the selected brackets may be precisely oriented on each crown model. The crown models with accurately attached brackets can then be moved from the "ideal" set-up back to the original mal-occlusion base, because the female portions of the simulated roots remain in the base of the original mal-occlusion. Thus the brackets are now positioned on each crown model and each crown model is back in its original mal-occluded position.

While the above apparatus and procedure facilitates precise positioning of brackets, it does require a number of procedural steps and is therefore relatively time consuming.

An indirect method for placement of brackets on a patient's teeth is disclosed in U.S. Pat. No. 3,439,421 to T. E. Perkowski. Perkowski discloses an orthodontic articulator that permits reassembly of cast crowns into a desired form of realignment under a glass plate that is inscribed with a line indicating an arch form. A bracket positioning gauge is also disclosed for use in conjunction with the articulator for positioning brackets on an "ideal" model comprised of repositioned individual crown models set up under the inscribed arch form on the glass plate in a wax base. Thus, individual adjustment of the crown models is accomplished in the above manner, using heated spatulas, etc.

The Perkowski bracket placement mechanism involves use of a base with a flat surface for sliding across a reference table surface. A bracket mounting arm is adjustably positioned on the sliding base with an extending pin that may be positioned by adjustment mechanisms to the desired level at which the various brackets are to be placed on the "ideal" set-up. Each bracket is received by the pin along the arch wire slot. The pin permits the bracket to pivot about the axis of the pin as the pin is moved in position to attach the bracket to an orthodontic metal band previously placed on the crown model. Orientation to the bracket slot is not controlled by the mounting arm but rather by the labial/buccal surface of the tooth model and curvature of the bracket backing, which may vary considerably. The curvature of the engaged surface may cause the bracket to pivot on the carrying pin to a position wherein the vertical wall of the slot is not perpendicular to the desired plane for the arch wire. Thus the arch wire will have to be adjusted in the buccal-lingual (torque) direction for each crown.

When an "ideal" set-up is made and that is, the crowns and gum section areas are "cut free" of the mal-occlusion cast, id becomes difficult and provides chances for inaccuracies to occur when transferring the brackets from the "ideal" set-up to the mal-occluded teeth in the patient's mouth. This is because the accurate transfer of the brackets relies on how the mal-occluded teeth approximate each other in the mal-occlusion. Thus "cutting free" each crown model to do an "ideal" set-up and then going back and rearranging the "cut free" crowns to the original mal-occlusion to facilitate transfer of the brackets from the cast to the patient's teeth obviously introduces numerous possible inaccuracies.

Therefore there is a need to obtain apparatus and procedures by which precision placement of brackets is afforded on a mal-occlusion cast model, without requiring separation of the individual crown models from the cast. A need also exists to eliminate tedious positioning of the individual crown models in an "ideal" set-up before proper positioning of the orthodontic brackets.

It is therefore an object of the present invention to obtain and record sufficient information relating to an "ideal" occlusion for each crown model in a dental cast without requiring that each individual cast crown model be cut away from the mal-occlusion cast. The crowns models are not separated from the cast and therefore remain in their original mal-occlusion orientation. Thus the difficult problem is resolved of later reproducing the mal-occlusion once the brackets are placed on the crown models. A cast model of the mal-occlusion must be available to facilitate transfer of brackets from the crown models to the actual crowns in the patient's mouth.

It is another object of the present invention to provide apparatus that may be used to progressively "lock in" each plane of space as it is selected in relation to an "ideal" set-up of the individual crown models in a mal-occlusion cast model. By doing so, one can alter one plane of space without losing or altering the other two planes. In other known systems, any correction of one plane can alter the other two planes. This is especially true of bracket positioning mechanisms that make use of single point pivotal mounts for the cast model in which, for example, torque is initially set and subsequent adjustments are made to locate the desired rotational position of the incisal edge and the angular position of the long axis of the crown model. In such systems it is not unusual to lose the initial torque setting while attempting to make adjustments for the incisal edge rotation and the long axis angulation adjustments.

It is a further object of the present invention to "index" an entire cast model such that a precise record is maintained on the mal-occlusion cast structure itself relating to the "ideal" set-up of the associated crown model in the cast. Such "indexing" allows for:

a) checking accuracy as a bracket placement tool is used to secure a bracket to the crown model;

b) placement of orthodontic brackets on the crown models at any time and at any place such as a dental laboratory or the office which the patient attends. This also facilitates accurate replacing of lost brackets that typically come off the patient's teeth during the continued course of treatment;

c) totally accurate placement of brackets by less skilled people. Fewer decisions are necessary with indexing and special placement instruments;

d) selection of a bracket height most suitable for each dental cast, which may be readily and uniformly done;

e) the rigidity of bracket placement which, in turn, allows for direct transfer tray construction either for individual or multiple teeth;

f) determining a selected bracket torque by instrumentation using the index rather than the "average" torque built into the bracket by the manufacturer. Thus, one is not required to rely upon the contour of the base of the orthodontic bracket to determine torque; and g) determination of the in and outs for the various teeth, again without reliance upon "standardized" brackets with an "average" thickening for various "in and outs" which has previously been concluded to be inaccurate due to the wide variation of tooth form and different bracket height selection by various Orthodontists.

The above and other objects and advantages will become apparent upon reading the following description and upon viewing the appended drawings.

BRIEF DESCRIPTION OF THE DRAWINGS

The preferred embodiment of the invention is illustrated in the accompanying drawings, in which:

FIG. 1 is a pictorial view of the present dental cast model, including the present index related to crown models and adjacent model gum tissues;

FIG. 2 is a pictorial view of a conventional orthodontic bracket;

FIG. 3 is a pictorial view of a cast mounting device and adjustment means;

FIG. 4 is an enlarged sectional view taken substantially along line 4—4 in FIG. 1;

FIG. 5 is a front end elevation view of the elements shown in FIG. 3;

FIG. 6 is a rear elevation view of the elements shown in FIG. 3;

FIG. 7 is a perspective view of a sighting device;

FIG. 8 is a fragmented side view of a height gauge on the sighting device in relation to a crown model;

FIG. 9 is a fragmented, enlarged end view of the vertical reticle of the sighting device in relation to a cast model;

FIG. 10 is a fragmented top plan view of a horizontal reticle of the sighting device;

FIG. 11 is a side elevation view of the cast mounting device, the adjustment means, and sighting device with a cast thereon being partially broken away;

FIG. 12 is a side elevation view of the cast mounting device, adjustment means, and a recording drill;

FIG. 13 is a side elevation view of a bracket holder and adapter for placing a bracket on a dental cast, the cast and bracket being shown by dotted lines;

FIG. 14 is a top plan view of the holder and adapter;

FIG. 15 is an end view as seen from the left in FIG. 14; and

FIG. 16 is an end view as seen from the right in FIG. 14.

DETAILED DESCRIPTION

The following disclosure of the invention is submitted in furtherance with the constitutional purpose of the Patent Laws "to promote the progress of science and useful arts" (Article 1, Section 8).

Orthodontic brackets 5 (FIG. 2), are provided in numerous configurations. However, each bracket 5 typically includes a base plate 6 adapted to be secured to a tooth crown. The base plate 6 includes a surface that is typically convex in an attempt to match the corresponding curvature of selected crowns.

A typical orthodontic bracket 5 also includes a precision groove 7 that is intended to receive and mount an orthodontic arch wire (not shown). The groove 7 includes a base 8 that is precisely oriented in relation to the base plate 6. The base 8 provides a reference surface used to determine proper precision positioning of the dental arch wire.

In the more accurate indirect orthodontic bracket placement practices, actual brackets 5 may first be placed on a plaster cast or "dental cast" of the patient's mal-occluded crowns before transfer or placement of similar brackets in the patient's mouth.

In presently known forms, the dental cast is a common "tool" utilized by many Orthodontists. Such casts accurately reproduce the crowns and portions of the adjacent gum tissues of a selected arch in the patient's mouth. Dental casts are used to facilitate analysis and record the patient's initial mal-occlusion. Additional casts made throughout the treatment will demonstrate the progressive repositioning of the teeth to their desired "ideal" occlusion.

A novel indexed dental cast 11 (FIGS. 1 and 4) is described herein, along with apparatus and processes for the purpose of producing the indexed cast 11, and for precisely placing orthodontic brackets on the cast 11.

Unlike the existing, conventional dental casts presently used in orthodontics, the present indexed cast 11 includes important data that facilitates future placement of orthodontic bracket 5 to selected crown model 12 in the indexed cast.

A brief description of the present indexed dental cast 11 will be given, first with reference to features common to all dental casts used for orthodontic purposes, then with reference to features unique to the present novel cast construction.

Early stages of construction of the present cast make use of techniques common to the formation of ordinary dental casts used in the indirect methods of orthodontic bracket placement. A flexible mold is made of the patient's crowns and areas of the gingiva or gums adjacent the subject crowns. The mold is pulled from the patient's teeth and wet plaster is poured into the mold cavities formed by the crowns and adjacent gum tissues. The mold is removed when the plaster solidifies. What remains is a dental cast with a precise duplication of the patient's crowns and adjacent gum tissues. The bottom surface of the cast is trimmed using a grinding wheel or abrasive belt so a flat surface 23 is formed approximately parallel to the occlusal plane of the adjacent crowns models 12.

A number of crown models 12 may be represented in the cast, making up the entire arch; either the lower (mandibular) arch or the upper (maxillary) arch.

Landmark surfaces on the individual crown models are important to the Orthodontist in determining proper bracket placement. One such surface on each of the forward or frontal crown models 12 of the cast are the incisal edges 13. Labial contours 18 on the forward crown models and buccal contours 19 on the rearward crown models also provide useful information.

Incisors and adjacent cuspids include such incisal edges 13. Rearward bicuspids and molars include cusp tips 14 and cusp ridges 15. For purposes of this disclosure, the incisal edges 13, and the cusp tip 14 and cusp ridges 15 will be referred to collectively as the "chewing edges".

A very important aspect of the present dental cast 11 is an index 35 (FIG. 4) for each of one or more selected crown models 12. The index 35 records certain information with respect to an "ideal" position of the adjacent mal-occluded crown model 12.

It is again noted that this "ideal" position is not typically shown by the crown model in the cast. Indeed, the crown model in the cast is much more likely to be mal-occluded and will appear as such. The "ideal" position need not be exhibited by the actual crown model in the cast. Instead, the "ideal" positions of the various crown models in the dental cast are identified by the index 35, and the crown models remain integral with the cast in their original mal-occlusion.

Advantageously, the index 35 is comprised of an "ideal" reference on the gum tissue model 22 that records very accurate information regarding an adjacent, usually mal-occluded crown model 12. The "ideal" reference physically represents an accumulation of several bits of information, each relating to an "ideal" orientation of the adjacent crown model 12.

Preferably, the "ideal" reference is provided in the form of a bore 37 (FIG. 4), or more preferably a pair of parallel bores 37 formed on parallel bore axes 38 for each selected crown model 12. The bore axes have direct angular relationships to upwardly adjacent crown models.

The angles of the bore axes relate to: (a) the "ideal" torque angles of the crowns; (b) the "ideal" angular rotation of the crown models about their individual tooth axes; and (c) the "ideal" mesial/distal angle of the long axis.

The individual bores 37 each extend to closed bore ends 39. The closed end 39 of each bore is precisely located in relation to the above crown model as part of the index which records information related to the correct in and outs position.

The vertical distance from the chewing surfaces (incisal edges, cusp tips, or marginal ridges) to the bores 37 are related to relative vertical height positions of the upwardly adjacent crown models 12 and to any selected bracket height positions thereon.

Apparatus and procedures for obtaining the present dental cast with the precision index 35, and placement of brackets using the index 35 may be more easily understood as described below.

A preferred apparatus 40 (FIG. 3) for producing the index 35 includes a cast mounting device 43. The cast mounting device 43 includes a plate 44 for receiving the bottom planar surface 23 of the dental cast. An attachment device such as a stud and nut assembly 45 is provided on the plate for securing the cast 11 in position with the bottom planar surface 23 in flush engagement with the complimentary flat surface of the plate 44.

An adjustment means 47 is provided for orienting the cast mounting device 43 in relation to a recording means 90 (FIG. 12) for producing the index 35. The preferred adjustment means 47 generally includes a first adjustment device 52 that supports the cast mounting device 43, and a second adjustment device 74 for alternatively mounting either recording means 90 (FIG. 12) or a sighting device 99 (FIG. 7).

The first and second adjustment devices 52, 74 are mounted to a common rigid frame 75. Devices 52, 74 are spaced apart by the frame 75 in positions thereon selected through a number of adjusting controls used to selectively and precisely orient the cast model in space.

In a preferred form the adjusting means includes a crown rotation adjusting control 58 (FIG. 5), provided to set incisal edge, and cusp tip and cusp ridges at "ideal" rotated positions. Control 58 includes appropriate rotational adjustment and locking devices such as the worm and wheel and set screw lock arrangement shown in FIG. 5 for enabling selective rotation and locking of the cast model 11 about a rotary axis "R".

A long axis adjusting control 61 is also provided and is selectively operable to set the long axis "L" of the crown model on the cast mounting device 43 in a precise mesial\distal angular position. In Orthodontics, this is referred to as "tip". The long axis adjusting control 61, like control 56, is comprised simply of a pivot clamp arrangement.

The adjustment means also includes a torque adjusting control 56 (FIG. 5), provided to selectively set an "ideal" torque orientation for the adjacent crown model. The preferred torque control 56 is comprised of a pivot clamp arrangement that will facilitate pivotal adjustment of the plate 44 about a substantially horizontal torque adjusting axis "T" (FIG. 3).

An in and outs reference control 64 is also provided for determining in and outs for each crown model on the dental cast. Control 64 includes an adjustable stop 65 on the second adjustment device 74 that, along with elements described below, will establish a relationship between the area of the chewing edges and the bore depth (location of each bore closed end 39) in the dental cast 11.

The second adjustment device 74 includes a platform 77 having a top reference surface 79. A precision guide groove or way 81 is formed in the top surface 79 of platform 77. The guide groove or way 81 is used to alternatively mount the recording means 90 or the sighting device 99.

The platform 77 is adjustably positionable by a spatial height adjusting control 83. Control 83 is part of the adjustment means 47, for determining a uniform height or a measured distance from an incisal edge, cusp tip, or marginal ridge of a selected crown model 12 to which all other crown models in the dental cast will be referenced to.

The platform 77 is also adjustable laterally by means of a lateral adjustment 86. A longitudinal adjustment 88 is substantially perpendicular to the lateral adjustment 86 to selectively move the second adjustment device 74 toward or away from the first adjustment device 52. Adjustments 83, 86, and 88 are, like the first adjustment device controls described above, comprised of screw or rack and pinion type adjusting arrangements that are relatively common to the work piece or tool adjustment arts.

It should also be understood that the adjustments found on the second adjustment device 74 could also be provided on the first adjustment device 52 and visa versa. Though such alternates are not shown, it is well within the scope of this disclosure to provide such arrangements.

All the above adjustment controls are relatively independent to facilitate individual adjustment of the crown models in three planes of space. Adjustments are completed and set successively with initial adjustments not being substantially effected by subsequent adjustments. The torque adjustment, for example, will not be substantially effected by the mesial distal angular adjustment, etc..

The several adjustments described herein are provided to set and lock various "ideal" angular positions of the crown model in space while the subject crown model remains in its original mal-occluded position in the cast model.

The recording means 90 is utilized for producing the index 35 adjacent a crown model 12 held in a selected "ideal" position through use of the above described adjustment features.

In a preferred form, the recording means 90 (FIG. 12) is comprised of a drill 92 for forming the bores 37 in the cast material forming the model gum tissue 22. Preferably, the drill includes two drill bits 93 for mounting a pair of drill shanks 94 in substantially parallel relation for producing the bores 37.

The drill 92 is preferably mounted to a drill base 97 that is movably mounted to the top surface 79 of platform 77. A guide 98 is provided on the base 97 and is slidably received within the precision guide groove or way 81 on the platform to precisely guide the drill in a translational path toward and away from the dental cast held on the cast mounting device 43.

The stop 65 of the in and outs reference control 64 is positionable via a set screw along a way 95 formed in the platform 77. The stop 65 selectively engages a complimentary fixed stop 96 on the drill base 97 in order to set a bore depth related to the chewing edge area of each crown model. This relationship of bore depth and the area of the chewing edge will facilitate determination of in and outs by a bracket holder 123 (described in greater detail below).

The relative adjusted positions of the first and second adjustment devices 52, 74 is determined through use of the sighting device 99. In general, the sighting device 99 includes a reference means 101 thereon for selective alignment with selected surfaces of a crown model to enable precise positioning of the crown model in space by operation of the first and second adjustment devices.

More specifically, the preferred sighting device 99 (FIG. 7) includes a base 106 with a guide bar 107 that is slidably received within the precision guide groove or way 81 (FIG. 9) of the second adjustment device. The base 106 mounts a vertical reticle 109.

The reticle 109 may be selectively magnified by a lens 110, along with an adjacent selected crown model on the cast mounting device 43. A sight groove 111 (FIGS. 7 and 9) is also utilized in conjunction with the vertical reticle 109. The vertical reticle 109 and sight groove 111 represent the "ideal" central axis of the adjacent crown model. The model may be positioned into selective alignment with the reticle 109 and sight groove 111 through operation of the long axis adjustment control 61.

The sighting device 99 also includes a horizontal reticle 113 (FIGS. 7 and 10) that is substantially perpendicular to the vertical reticle 109. In a preferred form, a lens 114 is positioned adjacent to the reticle 113 to visually amplify the adjacent contours of a crown model on the cast mounting device 43. The crown model may be moved into selective alignment with the reticle 113 through operation of the crown model rotation adjusting control 58.

Sighting device 99 further includes a height gauge 117. The height gauge 117 may be a relatively standard, conventional "dial indicator" gauge including a feeler rod 119 (FIG. 8). The feeler rod 119 extends to a end 120 that is adapted to engage selected surfaces of the adjacent crown model in order to record a distance from a vertical spatial point to the top surface 79 of platform 77. All remaining crown models on the dental cast will be positioned in a prescribed manner to this vertical spatial point.

As partially shown in FIG. 8, the feeler rod 119 is also used to establish a measured relationship between the area of the chewing edge of each crown model and the adjustable stop 65 on platform 77. The sighting device may be moved translationally to bring the tip of feeler rod 119 against the chewing edge of the adjacent crown model.

On lower teeth, the rod is positioned against the labial-buccal aspect of the chewing edge. On upper teeth, the rod should be positioned at the lingual aspect of the chewing edge.

With the rod tip in position against the appropriate area of the chewing edge, the user may set and lock the adjustable stop 65 on the platform 77 against a stop 122 on the base of the reference means 101. This establishes initial in and outs information to be included in the index by way of the depth of bore produced by the recording means and limited by the setting of stop 65. The feeler rod 119, base 106 and stops 65 and 122 therefore also constitute elements of the in and outs reference control 64.

The height gauge 117 further includes a lock-up knob 121 that facilitates selective elevational adjustment of the feeler 119 in an upwardly oriented storage orientation where the feeler is situated elevationally clear of the cast model.

The sighting device 99 is removably mounted to the second adjusting device 74 (FIGS. 9 and 11) in order to aid the user in determining precise angular and spatial orientations of the platform 77 in relation to a cast model held on the first adjustment device. The sighting device 99 is removable from the second adjustment means in order to facilitate mounting of the recording means 90 (FIG. 12), after the "ideal" angular positions and spatial orientation of each crown model is achieved. After each crown model is so positioned, the recording means 90 can be utilized to produce the index 35 on the cast model, thereby permanently recording the adjusted positional information obtained by operation of the first and second adjustment devices.

In preparation for the present indexing method and operation of the above apparatus, a standard dental cast is made of the patient's mal-occlusion. Preferably, an impression of the entire arch is made, using conventional known impression and casting techniques. The cast includes plaster models of the subject mal-occluded crowns and integral portions of the adjacent gingival tissues. The bottom surface and sides of the cast are trimmed if necessary to produce a bottom reference surface that is substantially parallel the occlusal plane of the crown models in the arch above. It is noted that the cast may be of either the upper maxillary arch, or the lower mandibular arch. For purposes of this disclosure, description will follow assuming the cast model is the lower mandibular arch.

Operation of the present apparatus and steps of the present method may commence with mounting the dental cast to the cast mounting device 43. This is done by securing the cast to the plate 44 through means of the stud and nut assembly 45. The bottom plane surface of the cast is thus held firmly against the plane reference surface of the plate 44.

Care is taken to mount the dental cast with the forward crown models of the cast roughly facing the second adjusting device 74. The various adjustments are then "zeroed out", with the surface 44 set in a horizontal, generally centered beginning position as shown in FIGS. 3, 5, and 6.

Next, a particular crown model is selected to be the first to be indexed. Preferably, the second bicuspid is first selected since the exposed crowns of the second bicuspids typically protrude the least distance above the gum line and therefore define a vertical "range" for the rest of the crown models in the cast within which brackets may be placed.

The sighting device 99 is mounted to the platform 77, with the guide bar 108 slidably received in the platform precision guide way 81. The various sighting devices are now in precise position to assist in precisely positioning the subject crown model in its "ideal" position in space (yet with the subject crown model still integrally joined with the remainder of the cast in its original mal-occluded position).

The user determines the "ideal" rotational position of the crown model, using the horizontal reticle 113 (FIG. 10). The user sights through the horizontal lens 114 and visually aligns the reticle 113 parallel to the cusp tip 14 and cusp ridges 15. This is done using the crown rotation adjusting control 58 by turning the control knob to correspondingly rotate the plate and the cast.

Next the user may utilize the vertical reticle 109 (FIG. 9) to aid in selecting the "ideal" angular mesial/-distal position for the long tooth axis. The crown model is moved by operation of the long axis adjusting control 61 (FIG. 11) to bring the appropriate surface indicia on the buccal surface of the crown model into visual alignment with the reticle 109. The control 61 and cast 11 are then secured in the selected "ideal" long axis position.

The desired torque is selected based on the torque present in the mal-occluded crown and the anticipated new position the crown will be moved to in treatment. This is done by observing, visually or mechanically, the buccal contour orientation of the selected crown model 12.

For purposes of this disclosure, an assumed "ideal" torque is the same torque that the lower bicuspid crown had in the mal-occlusion. Therefore, the torque adjusting control 56 is set to zero, using the available angle scale and pointer 57 in the side of the apparatus (FIG. 11). The control 56 is then secured, locking the torque adjustment.

The vertical height adjustment is next. This adjustment is made by placing the tip of the feeler 119 on the buccal cusp tip (FIG. 11) of the crown model. A reading of the gauge 117 is recorded. This reading is used to determine the "ideal" vertical position of the crown model in space. More specifically, the reading is related to the platform 79, to which all the remaining crown models of the dental cast will be vertically positioned to using the spatial height adjusting control 83. The reading thus recorded from the buccal cusp tip of the second lower bicuspid becomes the reading that all other crowns in the arch will be positioned in reference to.

The depth of bore 39 is next established to later determine in and outs. This is done again using the feeler rod 119. However this time the feeler rod 119 is moved by sliding the sighting device 99 toward the cast until the rod tip just touches the buccal area of the chewing edge of the crown model (FIG. 8). This position relates the area of the chewing edge to the stationary stop 122 and is recorded by adjusting and securing the stop 65 of the platform 77 in abutment with the stationary stop 122 on the base of the reference means.

The crown model is now located: (a) in its "ideal" position in three planes of space, (b) at a selected vertical height, and (c) with recorded initial in and outs reference relating the area of the chewing edge and the bore depth (location of the bore closed end 39) in the dental cast 11, even though the crown model remains integral with the remainder of the cast and in its original mal-occlusion.

The sighting device 99 is now removed from the platform 77.

Next the recording means 90 is mounted to the platform 77 (FIG. 12), with the guide 98 slidably received in the precision groove 81. This precisely orients the drill 92 in position to produce the precision index 35 in the cast below the crown model. As the drill is moved forwardly, the drill tips engage and begin boring into the plaster cast material. The drills stop as the stationary stop 96 on the drill base comes into contact with the pre-set stop 65 on the platform base 77.

The parallel axes of the bores 37 are thus precisely oriented and carry, in their spatial and angular orientation in relation to the crown model, the index information relating to the desired "ideal" position of the crown model. The depth of the bores relate to a specific area of the chewing edge. This relationship will facilitate determining the in and outs with the bracket holder 123.

The crown model is thus precisely indexed in a relatively permanent manner with the information of the index relating to the "ideal" position of the crown model, even though the actual crown model has not changed position at all in relation to the remainder of the crowns in the cast. In fact the crown model remains integral with the cast in its original mal-occlusion. The index facilitates precise positioning of an orthodontic bracket on the crown model and the cast itself is further useful to enable transfer of the bracket to the patient's mouth using known transfer tray techniques. Additionally, with the present index, the original mal-occlusion is constantly available for reviewing progress during treatment. The index further enables placement of brackets at any time and at nearly any location by relatively moderately skilled personnel.

The above description relates to the operation, method, and apparatus for producing the index in a dental cast for a single crown model in the cast. It should be understood that the above apparatus and process steps may be repeated successively on each crown model of the cast so a precision index may be provided for every crown model in the entire dental cast.

Description will now be given relative to apparatus for mounting an orthodontic bracket to the indexed dental cast, using the index as a precision guide for precise bracket placement.

A bracket holder 123 is shown in detail by FIGS. 14–16 of the drawings. The holder includes a plate 124 for receiving the precision slot 7 of the bracket 5. An end surface 125 of the plate 124 is adapted for flush abutment with the base 8 of the bracket precision slot 7. The plate 124 is situated at the end of an elongated shaft 127, provided with in and outs measurement indicia 128 along its length.

The shaft 127 is adjustably mounted to an adapter means 129 for orienting the bracket holder 123 to hold a bracket 5 thereon in a placement position against the crown model 12 that relates specifically to the index 35.

Adapter means 129 includes a height of bracket adjustment 136. Adjustment 136 facilitates selective adjustment of a bracket placement height relative to the incisal edges, cusp tips, or marginal ridges. The gum line on the crown models can limit the selected bracket height on the dental cast.

Generally, the bracket is placed in about the middle of the actual crown height and this is referred to as "bracket height". However, on a dental cast a "clinical crown height" is the amount of the crown model that protrudes through the gum tissue. Therefore, often because the crown has not protruded or "erupted" a great deal as yet, many brackets are placed close to the gum line on such crowns.

The preferred adapter means also includes an angle adjustment means 132 for selectively setting a tip angle of the bracket of the bracket holder 123. The adapter angle adjustment means advantageously includes a tubular sleeve 137 that slidably and rotatably mounts the shaft 127. A gauge plate 140 is mounted to the tubular sleeve 137 and a pointer 141 is mounted to the shaft 127 adjacent the gauge plate 140. The tubular sleeve 137 also includes an end edge 142 that is useful in conjunction with the indicia 128 on the shaft to determine desired in and outs distances.

The height of bracket adjustment 136 includes a threaded stud 143 mounted to the tube. The stud 143 includes an upright slot 145 (FIG. 15). A nut 146 is threadably engaged on the threaded stud 143. The nut 146 and threaded stud 143 comprise the height of bracket adjustment 136. Rotation of the nut 146 results in corresponding upward of downward movement of the bracket holder 123.

This movement is made in precise relation to a pair of probes 147 that are spaced apart at a fixed distance that is equal to the spacing of bores 37. The fixed probes are loosely received in the slot 145 of the threaded stud 143. The probes are therefore free to move up and down relative to the bracket holder 123.

The probes are joined by parallel upright guide sleeves 148 that slidably receive guide pins 149 on the tubular sleeve 137. One of the pins 149 may be supplied with indicia 150 to identify a selected bracket height.

The probes 147 also include forward probe ends 152. The ends 152 are adapted to be inserted into the bores 37 and to abut the closed bore end 39 to assist in determining the in and outs position along with the in and outs indicia 128 on the shaft 127.

The bracket 5 may be placed on the indexed cast, firstly by placing the bracket on the plate 124 with the bracket slot base 8 and plate end surface 125 in abutment. The bracket is thus held securely in a precision position relative to the adapter means 129.

The probes 147 are then pressed into the bores 37, to the closed bore ends 39. This automatically positions the bracket holder 123 at the precise angular orientation set by the index, which as described above includes the previously selected "ideal" torque, rotational angle and mesial distal long axis angle information. It also places the bracket holder 123 in a precise reference position for vertical height and for initial in and outs adjustment considerations as the bracket 5 is positioned adjacent the crown model 12.

The probes 147, in place within the bores 37, hold the bracket holder 123 in precise position while enabling the shaft 127 to be moved to position the bracket 5 against the crown model 12. The shaft 127 is slid forward until the bracket base plate 6 approaches the buccal surface 19 of the crown model 12.

The vertical height nut 146 is then adjusted until the bracket 5 is at the desired vertical height ("bracket height") on the buccal surface 19 of the crown model 12. The operator then records the vertical height information by reading the indicia 150 in relation to a top reference edge 151 on the adjacent guide sleeve 148. This vertical height ("bracket height") becomes the vertical height or reference point for all the remaining crown models 12 on the cast 11.

The second bicuspids seldom require "tipping" adjustment. However for purposes of this disclosure a "tip" of say 6 degrees will be assumed. Thus the shaft 127 is rotated 6 degrees, bringing the pointer 141 into alignment with the 6 degree indicia on the gauge plate 140. The desired "tip" angle is thus set. Uniquely, the bracket holder 123 pivots the bracket at the center of the bracket slot base 8 so that the selected bracket height is not altered as the bracket is tipped.

The last adjustment is for in and outs. When all selected crown models have been indexed to record their "ideal" positions, with the "ideal" torque, rotation, long axis, and height determined for each, it becomes possible to determine the actual in and outs that exist for the crown models at any selected bracket height.

Certain teeth typically require at least some in and out correction. For example upper centrals and upper laterals often need such correction. Again, for purposes of the present disclosure it will be assumed that an in and outs adjustment is also needed for the second bicuspid.

First it is understood that the depth of the bores 37 to the closed ends 39 initially relate the position of the labial-buccal area of the chewing edges for lower teeth or the corresponding lingual area on the chewing edges of the upper crowns.

The thickness of the individual dental crowns and of adjacent crowns in a dental arch vary considerably. Yet in an "ideal" dental arch, the chewing edges line up in a continuous arch line. The orthodontic brackets are placed 4-6 mm vertically from the chewing edges on the labial\buccal surfaces of the dental crowns. These labial buccal surfaces do not line up to form a continuous arch line. An irregular arrangement of label\buccal surfaces are present due to the various crown thicknesses and contours of the crowns in the areas to receive the brackets.

To compensate for this, brackets of various thicknesses are selected which in turn will result in a continuous arch line of the precision slot 7 of the orthodontic bracket 5.

Thus the term "in and outs" refers to the irregular arrangement of the labial/buccal surfaces to which the orthodontic brackets will be affixed to.

To establish the continuous arch line for the precision slots, each bracket must be carefully selected and precisely positioned on the crown model. To do this, an in and outs reference distance is first obtained. This is accomplished by selecting an appropriate bracket 5, which is then placed on the plate 124.

The next step involves inserting the probes 147 into the index bores 37 of a crown model having a prominent buccal-label surface. In the instance of the lower second bicuspid, the adjacent prominent buccal surface would be that of the adjacent first molar. The probes are inserted into the bores 37 below the adjacent first molar until the probe ends 152 touch the bore closed ends 39. This automatically sets the adapter means in reference with the chewing edge of the adjacent molar.

Next the shaft (which has previously been adjusted for a selected bracket height using the bracket height reference established above) is moved inwardly to bring the bracket into contact with the prominent buccal surface of the selected molar. The indicia 128 on the shaft 127 then in alignment with the end edge 142 of the tubular sleeve 137 represents a "zero" marking from which the in and outs of the adjacent bicuspid is to be gauged. This "zero" position indicates the proper in and out position of the bracket slot base 8 at the selected bracket height, to the less prominent buccal surface of the adjacent second bicuspid in that arch.

Next, the adapter is removed and re-inserted into the index bores 37 below the second mandibular bicuspid. An appropriate bracket is placed on the plate 124 and the shaft is moved to the previously noted "zero" marking. If a spaced exists between the bracket base plate 6 and the buccal surface 19 of the crown model or if the bracket base plate contacts the buccal surface 19 of the crown model before the "zero" reading is obtained, a bracket of appropriate thickness will have to be selected. Otherwise appropriate measures will be required to match the bracket thickness to set the bracket slot base 8 at the desired in and out position. Such "appropriate measures" may include the use of shims between the bracket base and the crown model, or the use of adhesive to "fill the gap" between the bracket base and the adjacent surface of the crown model.

Once all the brackets have been accurately placed on all selected crown models of the dental mal-occluded cast, a procedure to transfer these brackets to the patient's teeth is desirable. Two possible procedures to transfer the precision brackets positions to the patient's teeth will be discussed.

Firstly, a dental compound, softened by being placed in hot water can be placed on the crown model 12 and pressed about adjacent models along their incisal edges and on the bracket 5. This is done with the bracket holder 123 in position, holding the bracket 5 in the precision position selected as described above.

The compound hardens in seconds to thereby form an individual transfer tray, enabling direct transfer of the bracket to the patient's mouth. It may be noted that the bracket may be held in position by the bracket holder during application of the softened dental compound. Thus the bracket needn't be attached to the crown model prior to the transfer. To transfer the bracket to the patient's mouth, the then hardened dental compound and captured bracket are removed from the cast.

A spot of adhesive is applied to the bracket base plate. The hardened dental compound and the bracket are then seated on the same crowns in the patient's mouth. The adhesive will cure shortly. The compound can then be softened by hot air and removed from the bracket and the patient's teeth. This leaves the bracket precisely positioned on the patient's crown.

The above steps may be repeated for each bracket to be placed in the patient's mouth. More than one bracket may be transferred at a time, providing an equal number of the bracket holders are used.

A second alternative available to the practitioner is to secure the correctly positioned bracket to the crown model by an adhesive. The bracket holder is then removed from the bracket slot, leaving the bracket on the crown model.

A transfer tray can then be produced, using techniques commonly used in indirect transfer methods. The bracket may thus be transferred from the crown model to the patient's mouth.

Alternatively, an impression of the bracket may be made in flexible mold material, along with the crown models. Second brackets are then placed in the bracket impression. Adhesive is applied to the second brackets and the impression material is placed over the same crowns in the patient's mouth. The brackets are automatically precisely positioned by the impression material and will become adhered to the actual crowns. Of course this procedure may be used to transfer as little as one bracket at a time or an entire arch of brackets may be transferred in this manner.

In compliance with the statute, the invention has been described in language more or less specific as to structural features and process steps. It is to be understood, however, that the invention is not limited to the specific features shown, since the means and construction herein disclosed comprise a preferred form of putting the invention into effect.

For example, it is pointed out that the apparatus and processes described herein may be performed as described or by using control and robotic technology. Thus the process steps (at least those involved in producing the index) could be automated. For example, the sighting device could make use of optical scanning technology and corresponding robotic controls could be used to position a dental cast to record the index information identified above. The only manual steps remaining would then be using the adapter means to position the brackets and the steps involved in transferring the brackets to the patient's mouth.

The invention is, therefore, claimed in any of its forms or modifications within the proper scope of the appended claims appropriately interpreted in accordance with the doctrine of equivalents.

I claim:

1. A crown model position recording apparatus for recording position and orientation of a crown model in a dental cast:
   a cast mounting device adapted to securely hold a dental cast in a selected orientation;
   recording means for positioning a physically-engageable locator on the dental cast; and
   adjustment means for positioning the recording means relative to the dental cast to precisely relate the position of the locator on the dental cast to the position and orientation of a crown model in the dental cast.

2. The crown model position recording apparatus of claim 1 wherein the adjustment means includes:
   a crown rotation control for setting and holding a selected crown model at a prescribed rotated position in relation to the recording means;
   a torque adjusting control, independent of the crown rotation control, for setting and holding the selected crown model at a prescribed torque position in relation to the recording means;
   a long axis adjusting control, independent of the torque adjusting control and the crown rotation control, for setting and holding the selected crown model at a prescribed long axis angular position in relation to the recording means;
   a height adjusting control independent of the remaining controls for setting and holding the relative elevational positions of the dental cast and the recording means; and
   an in and outs reference control selectively operable to control the recording means to produce an in and outs reference.

3. The crown model position recording apparatus of claim 2 wherein the dental cast includes model gum tissue adjacent the crown model, the recording means being for positioning the physically-engageable locator on the model gum tissue, said locator being oriented thereon adjacent the selected crown model.

4. The apparatus of claim 2 wherein the dental cast includes model gum tissue adjacent the crown model, the recording means including drill for forming a bore in the model gum tissue, said bore being oriented in a prescribed relationship to the crown model.

5. The apparatus of claim 1 wherein the dental cast includes model gum tissue adjacent the crown model, the recording means being for positioning the physically-engageable locator on the model gum tissue.

6. The apparatus of claim 1 wherein the adjustment means includes a first adjustment device mounting the cast mounting device for selected positioning, and a second adjustment device for releasably mounting the recording means.

7. The apparatus of claim 6 wherein the first adjustment device includes a torque adjusting control selectively operable to set the torque of a selected crown model to a prescribed torque position in relation to the recording means.

8. The apparatus of claim 6 wherein the first adjustment device includes a crown rotation adjusting control selectively operable to set the incisal edge, or cusp tip ridges of a selected crown model in the dental cast at a prescribed rotational position in relation to the recording means.

9. The apparatus of claim 6 wherein the first adjustment device includes a long axis adjusting control selectively operable to set the long axis of the crown model at a prescribed long axis position in relation to the recording means.

10. The apparatus of claim 6 wherein the second adjustment device includes an in and outs reference control selectively operable to control the recording means to produce an in and outs reference on the cast relating to the selected crown model.

11. The apparatus of claim 6 wherein the second adjustment device includes a height adjusting control for setting and holding the relative elevational positions of the dental cast and the recording means.

12. The apparatus of claim 6 wherein the first adjustment device includes:
   a crown rotation adjusting control selectively operable to set the incisal edge, or cusp tip ridges of the selected crown model at a prescribed rotation position in relation to the recording means;
   a long axis adjusting control selectively operable to set the long axis of the selected crown model at a prescribed long axis angular position in relation to the recording means;
   a torque adjusting control selectively operable to set the torque of a selected crown model to a prescribed torque position in relation to the recording means;
   wherein the second adjustment device includes a height adjusting control for setting and holding the relative elevational positions of the dental cast and the recording means; and
   wherein the second adjusting control includes an in and outs reference control selectively operable to control the recording means to locate an in and outs reference on the cast related to a selected chewing surface of the selected crown model.

13. The apparatus of claim 1 wherein the recording means comprises a boring device having two drill bits for mounting drill shanks in substantially parallel relation for boring index holes into the dental cast on bore axes and to bore depths determined by the adjustment means.

14. The apparatus of claim 1, wherein the adjustment means is further for relating the position of the locator to the crown model in three dimensions.

15. In a dental cast:
   a cast body formed of a molded material;
   a mal-occluded crown model on the cast body; and
   a physically-engageable locator which is positioned directly on the cast body adjacent the mal-occluded crown model, said locator being spatially and angularly positioned to correlate with the spatial and angular position of the crown model.

16. In a dental cast as claimed by claim 15, wherein the locator comprises a bore formed into the cast body.

17. The dental cast as claimed by claim 15, wherein the locator comprises a pair of parallel bores formed into the cast body.

18. The dental cast of claim 15 wherein the locator is oriented in relation to the mal-occluded crown model to include information relating to the crown model's rotated position, torque position, long axis position, the vertical height position, and an in and outs reference.

19. In a dental cast as claimed by claim 15, further comprising:
   model gum tissue on the cast body adjacent to and integral with the mal-occluded crown model;
   wherein the locator comprises a bore formed into the model gum tissue.

20. In a dental cast as claimed by claim 15, wherein the locator correlates in three-dimensions to the spatial and angular position of the crown model.

* * * * *